June 11, 1963 C. H. FISCHER Plant Pat. 2,262
GLADIOLUS PLANT
Filed June 25, 1962
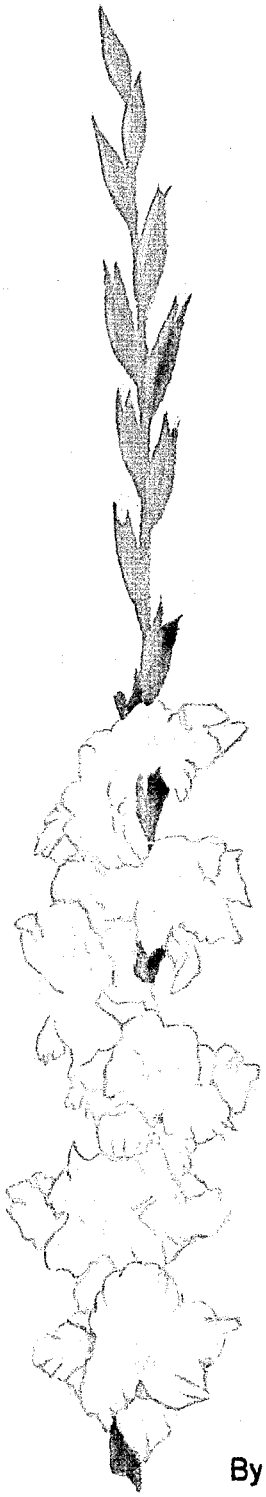
INVENTOR
Carl H. Fischer
By: Lamont Johnston
ATTORNEY United States Patent Office Plant Pat. 2,262
Patented June 11, 1963

2,262
GLADIOLUS PLANT

Carl H. Fischer, St. Charles, Minn., assignor to Selected Glads, Inc., New Albany, Ind., a corporation of Tennessee Filed June 25, 1962, Ser. No. 205,138
1 Claim. (Cl. Plt.—85)

My present invention relates to a new and improved variety of gladiolus plant and is notable particularly for its small size, intensity of color, ease of propagation and robust health. I have identified this new variety as seedling No. 306–55 in my breeding work.

To the best of my knowledge, this new variety is the result of a cross between the varieties Statuette (unpatented) and Little Gold (unpatented). Statuette was the seed parent and Little Gold the pollen parent. Hand cross pollination was done by me in my field at St. Charles, Minnesota, but no precaution was taken to prevent admixture of other varieties by bees or insects.

The new variety has been axially asexually reproduced by me in Minnesota by natural increase from cormels through several generations and its characteristics have proven to be permanently fixed.

The illustration, made a part of this application, shows a single bloom spike of this new variety, reduced in size, and is as nearly true to color as it is possible to depict. The illustration shows the arrangement of the florets on the stem and the shape of the florets. It also shows quite accurately the intense yellow coloring.

The color plate references, in the following detailed description, are to the "Horticultural Colour Chart," by the British Colour Council. Where there are other references to color, the ordinary dictionary meanings of the terms are intended.

*The Plant*

Growth: Extremely vigorous, bloom spike averaging 42 inches in height over-all. Prolific propagator.

Blooming: The variety is a mid-season bloomer, blooming in about 80 days from large bulbs. Each spike opens from six to seven 2¾ inch florets at one time. Successive blooms open, totalling an average of seventeen to eighteen florets to each spike.

Stems: Willowy. Average diameter at base is ¼ inch. Back of stem on flowerhead is reddish brown.

Foliage: Deep green; plants very erect. Average leaf is 1 to 1½ inches wide. Plant foliage, excluding the flower spike, is 24 inches high.

Disease resistance: This variety is very resistant to disease. It has been found resistant to Sclerotina dry rot, Septoria leaf spot and Fusarium yellows, diseases to which many other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases, whereas this variety remained healthy and unaffected.

Corms: Healthy and very round. Average 2 inches in diameter from adult plants. Husks are smooth and thin, with a strong purple tint around the top. Flesh is Buttercup Yellow $5/_2$.

*The Flower*

Spike: Wiry; has seventeen to eighteen buds and opens six to seven florets at one time.

Bud:

*Size.*—Opening buds are 2 inches long.

*Opening.*—Six to seven open at one time with five showing color.

Flower:

*Arrangement.*—Flowers are alternately spaced on the spike and all face in the same direction.

*Size.*—Lower blooms average 2¾ inches across when permitted to bloom on the plant in the field. Upper blooms are progressively smaller.

*Form.*—Lower petals are wide open while the upper petal is hooded. Florets are slightly ruffled.

*Keeping qualities.*—Average.

Petals:

*Shape.*—Petals are pointed and slightly ruffled.

*Size.*—Larger petals are 1½ inches across; lip petal is 1 inch.

*Aspect.*—Substance is heavy and the surface is smooth with slight ruffling at edges.

*Fragrance.*—None.

*Color.*—Color of the open floret is Empire Yellow 603. Bud is Primrose Yellow 601. Inside calyx and reverse of calyx are Fuchsine Pink $627/_2$.

Reproductive organs:

*Stamens.*—Empire Yellow $603/_2$.

*Pistils.*—White.

*Comparisons*

My new variety resembles Little Gold (unpatented) more than any other known variety, but differs from it principally as follows:

(1) My variety is more yellow than Little Gold.
(2) My variety opens better than does Little Gold.
(3) My variety has straighter stems.
(4) My variety opens more florets.
(5) My variety is more prolific.

Having thus disclosed my invention, I claim:

The new and distinct variety of gladiolus plant, substantially as herein shown and described, characterized by its intense yellow blossom color, ease of propagation and robust health.

No references cited.